US010881429B2

(12) United States Patent
Dickinson et al.

(10) Patent No.: US 10,881,429 B2
(45) Date of Patent: Jan. 5, 2021

(54) METHOD FOR THE PERCUTANEOUS CREATION OF AN ARTERIOVENOUS FISTULA (AVF)

(71) Applicant: STENT TEK LIMITED, Chelmsford (GB)

(72) Inventors: Robert Dickinson, London (GB); Sorin Popa, London (GB)

(73) Assignee: STENK TEK LIMITED, Chelmsford (GB)

( * ) Notice: Subject to any disclaimer, the term of this patent is extended or adjusted under 35 U.S.C. 154(b) by 501 days.

(21) Appl. No.: 15/683,049

(22) Filed: Aug. 22, 2017

(65) Prior Publication Data

US 2018/0000512 A1    Jan. 4, 2018

Related U.S. Application Data

(63) Continuation of application No. PCT/US2016/021782, filed on Mar. 10, 2016.
(Continued)

(30) Foreign Application Priority Data

Mar. 10, 2015 (GB) .................................. 1504060.3
Jul. 3, 2015 (GB) .................................. 1511692.4

(51) Int. Cl.
*A61B 34/20* (2016.01)
*A61B 17/34* (2006.01)
(Continued)

(52) U.S. Cl.
CPC .......... *A61B 17/3403* (2013.01); *A61B 17/11* (2013.01); *A61B 17/3415* (2013.01);
(Continued)

(58) Field of Classification Search
CPC . A61B 17/11; A61B 17/3403; A61B 17/3415; A61B 17/3421;
(Continued)

(56) References Cited

U.S. PATENT DOCUMENTS 5,830,222 A    11/1998 Makower
2004/0078046 A1    4/2004 Barzell et al.
(Continued)

FOREIGN PATENT DOCUMENTS

CN    102272556 A    12/2011
CN    102294896 A    12/2011
(Continued)

OTHER PUBLICATIONS

International Search Report and Written Opinion dated Jun. 30, 2016 in International Application No. PCT/US2016/021782.
(Continued)

*Primary Examiner* — Kai H Weng
(74) *Attorney, Agent, or Firm* — Perkins Cole LLP; Viola T. Kung; Alberto Araiza

(57) ABSTRACT

This document relates to the apparatus and methods used in the minimally invasive creation of arteriovenous fistula (AVF). In particular, the invention relates to the creation of an AVF using catheters and an alignment methodology that is based upon detection of asymmetric electric fields. The invention finds particular application in vascular access (VA) in the hemodialysis (HD) population.

17 Claims, 10 Drawing Sheets

Related U.S. Application Data

(60) Provisional application No. 62/209,153, filed on Aug. 24, 2015.

(51) Int. Cl.
*A61B 17/11* (2006.01)
*A61M 1/36* (2006.01)
*A61B 17/00* (2006.01)
*A61B 90/00* (2016.01)
*A61M 25/01* (2006.01)
*A61M 25/09* (2006.01)

(52) U.S. Cl.
CPC .......... *A61B 17/3421* (2013.01); *A61B 34/20* (2016.02); *A61M 1/3655* (2013.01); *A61B 2017/00867* (2013.01); *A61B 2017/1107* (2013.01); *A61B 2017/1132* (2013.01); *A61B 2017/3413* (2013.01); *A61B 2034/2053* (2016.02); *A61B 2090/0811* (2016.02); *A61B 2090/3925* (2016.02); *A61B 2090/3958* (2016.02); *A61B 2090/3966* (2016.02); *A61M 25/09* (2013.01); *A61M 2025/0166* (2013.01)

(58) Field of Classification Search
CPC .. A61B 2017/00867; A61B 2017/1107; A61B 2017/1132; A61B 2017/3413; A61B 2034/2053; A61B 2090/0811; A61B 2090/3925; A61B 2090/3958; A61B 2090/3966; A61B 34/20; A61M 1/3655; A61M 2025/0166; A61M 25/09
See application file for complete search history.

(56) References Cited

U.S. PATENT DOCUMENTS

| | | | |
|---|---|---|---|
| 2008/0171944 A1 | 7/2008 | Brenneman et al. | |
| 2008/0194939 A1 | 8/2008 | Dickinson et al. | |
| 2009/0096443 A1 | 4/2009 | Anderson | |
| 2010/0230588 A1* | 9/2010 | Atkinson | H01J 49/40 250/283 |
| 2011/0060264 A1 | 3/2011 | Porter et al. | |
| 2011/0316940 A1 | 12/2011 | Nakakubo | |
| 2013/0317334 A1 | 11/2013 | Bar-tal et al. | |
| 2014/0221803 A1 | 8/2014 | Bar-tal et al. | |
| 2015/0223729 A1 | 8/2015 | Balachandran et al. | |
| 2015/0374486 A1* | 12/2015 | Dickinson | A61B 17/11 623/1.14 |
| 2016/0045133 A1 | 2/2016 | Balachandran et al. | |
| 2018/0000512 A1 | 1/2018 | Dickinson et al. | |

FOREIGN PATENT DOCUMENTS

| | | |
|---|---|---|
| CN | 102939051 A | 2/2013 |
| EP | 1891895 A1 | 2/2008 |
| EP | 2528503 A1 | 12/2012 |
| JP | 2008511414 A | 4/2008 |
| JP | 2013248388 A | 12/2013 |
| WO | 9713463 A1 | 4/1997 |
| WO | 9713471 A1 | 4/1997 |
| WO | 0045886 A2 | 8/2000 |
| WO | 02/062265 A2 | 8/2002 |
| WO | 2006/027599 A1 | 3/2006 |
| WO | 2006026687 A2 | 3/2006 |
| WO | 2008/092246 A1 | 8/2008 |
| WO | 2008/097767 A2 | 8/2008 |
| WO | 2010052480 A2 | 5/2010 |
| WO | 2011092613 A1 | 8/2011 |
| WO | 2011159621 A2 | 12/2011 |
| WO | 2014/005155 A1 | 1/2014 |
| WO | 2014/137830 A1 | 9/2014 |

OTHER PUBLICATIONS

Combined Search and Examination Report dated Apr. 26, 2016 in UK Application No. GB1604107.1., dated Apr. 26, 2016.
European Search Report dated Nov. 15, 2018 for European Application No. 16762517.7, dated Nov. 15, 2018.

* cited by examiner

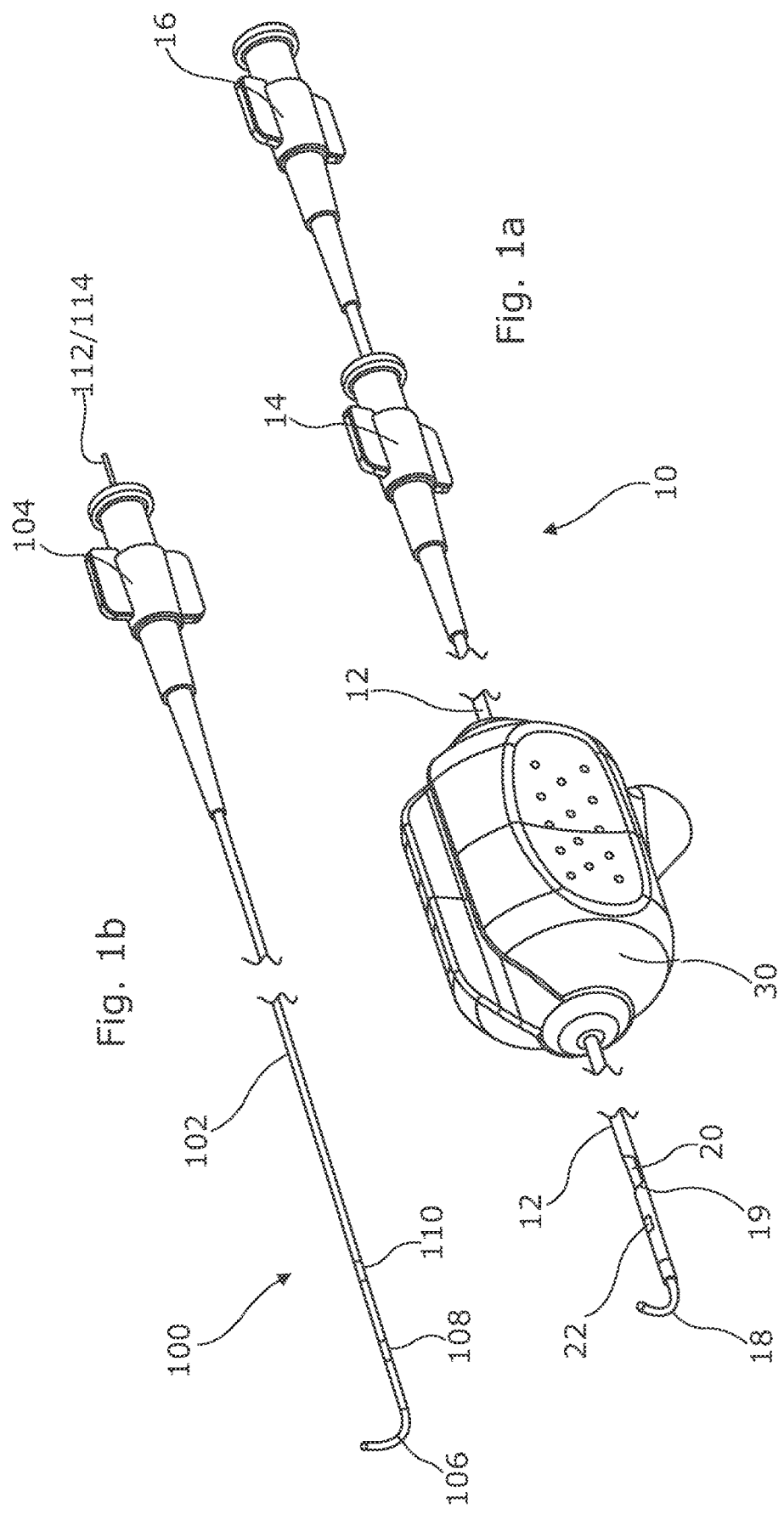

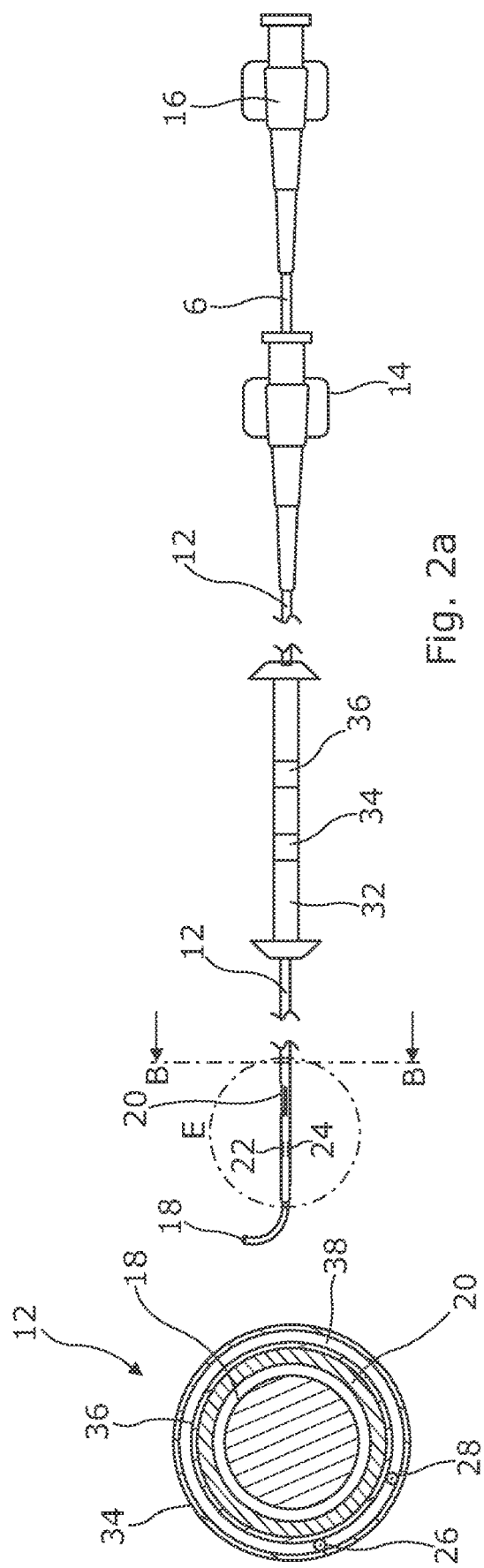
Fig. 2a
Fig. 2b
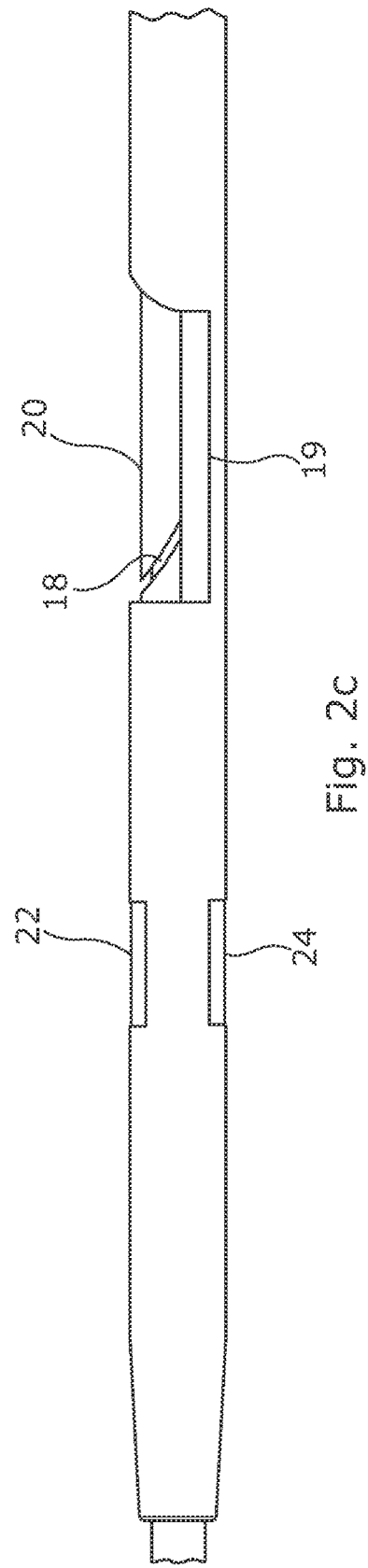
Fig. 2c

METHOD FOR THE PERCUTANEOUS CREATION OF AN ARTERIOVENOUS FISTULA (AVF)

This application is a continuation of PCT/US2016/021782, filed Mar. 10, 2016; which claims priority of GB1504060.3, filed Mar. 10, 2015; GB1511692.4, filed Jul. 3, 2015; and U.S. Provisional Application No. 62/209,153, filed Aug. 24, 2015. The contents of the above-identified applications are incorporated herein by reference in their entirety.

FIELD

The invention relates to the apparatus and methods used in the minimally invasive creation of arteriovenous fistula (AVF). In particular, the invention relates to the creation of an AVF using catheters and alignment methodology. The invention finds particular application in vascular access (VA) in the hemodialysis (HD) population.

BACKGROUND

More than half a million patients in the US and Western Europe whose kidneys are failing and need to undergo hemodialysis face a significant risk. This risk is due to the limitations and performance issues of current methods for a dialysis machine to connect to a patient's circulatory system known as a vascular access (VA) site. Achieving long-term vascular access which remains patent and infection free is very difficult. (See Leermakers et al. (2013); US Dept. Health and Human Services Report (2014); and Al-Jaishi et al. (2014)).

Vascular access can be achieved in one of three ways: arteriovenous prosthetic grafts (AVG), tunneled central vein catheter, or native arteriovenous fistula (AVF). The main function of both the AVF and the AVG is to create a "short circuit" in the peripheral vasculature by directly connecting high-pressure arterial flow and low-pressure venous flow. This results in a greatly increased flow rate, which is necessary for dialysis, in the graft or the vein. The latter also enlarges and arterializes making it easier to cannulate.

Currently a patient requires open surgery with local or general anesthesia to receive an AVF. Once the AVF has been created one needs to wait until it matures and is ready to be used for hemodialysis (HD). VA's can fail due to a variety of reasons including thrombosis, stenosis, infection, or neointimal hyperplasia. Overall, there is a need for a VA which is easy to implant, matures quickly and has a high patency rate.

Minimally invasive surgery is a common method to perform a variety of cardiovascular procedures. It is typically performed using catheters that are inserted into various lumens within the body through small incisions in the skin. A percutaneous approach to AVF creation has several clinical benefits including simplifying the procedure and reducing surgical trauma to the vessels which has a negative effect on patency.

Several technologies have been developed with the purpose of creating an arteriovenous fistula percutaneously however none have been approved for clinical use. All of the following technologies employ one or two catheters in order to create an anastomosis between two adjoining blood vessels. U.S. Pat. No. 8,523,800 describes technology for forming a fistula with the aim of treating COPD patients and those with hypertension. U.S. Pat. No. 5,830,222 and WO2006/027599 describe technology for percutaneously connecting two vessels to divert arterial blood to the venous system, and U.S. Pat. No. 6,475,226 describes an alternative to coronary bypass surgery. US2013/0281998 and US2012/0302935 describe technologies for percutaneously creating fistulas for dialysis use.

There are several suitable anatomical locations for the vascular anastomosis which allow for the formation of a vascular access site suitable for haemodialysis. The most commonly used include in the radial artery and cephalic vein at the wrist level, the brachial artery and cephalic vein at the antecubital fossa, and the brachial artery and basilic vein in the upper arm. Less commonly a fistula can be created in the upper leg between the saphenous vein and femoral artery.

There are two main approaches to using intravascular catheters for creating the anastomosis; one technique involves placing a tube or stent graft between the two vessels in order to form the connection, the other creates a hole directly between the two vessels where they are close together. Implementing either technique requires an active means to align the two catheters, as fluoroscopy is not adequate for the angular alignment. Accurate alignment is more important in the first case when the ratio of the vessel separation to the vessel diameters increases.

Several different modalities for radial alignment have been presented in the literature and typically include a transmit catheter sending a signal toward a receive catheter which measures the magnitude of the signal and relays that information as an indication of alignment. Different types of signals include ultrasound (see, for example, WO2006/027599, US2004/0133225), light (see, for example, U.S. Pat. No. 6,475,226), and inductive fields (see, for example, EP1377335). However, a drawback of such methods is that they require relatively complex mechanical or electronic transducers, to generate and receive the signals, which can be difficult and expensive to manufacture and limit the size of the catheters, in particular their suitability for use in smaller diameter vessels.

SUMMARY

The present invention provides methods and apparatus for improving the performance of a percutaneous surgical AVF procedure over the prior art methods using an alignment method based in some embodiments upon detection of a directional signal such as, but not limited to, electric field orientation. This invention allows for the creation of a percutaneous AVF via a system and apparatus that comprises two catheters which are smaller, cheaper to produce, and easier to operate than those provided in the prior art. In particular, the method described applies to the creation of an AVF for use as VA in hemodialysis patients.

Accordingly, in a first aspect the invention provides a method for improving venous access in a patient in need thereof by creating a fistula between a first vessel and a second vessel, the method comprising the steps of:

a) inserting, via a percutaneous route, a first device into the first vessel, wherein the first device comprises a catheter that comprises a directional signal source, and wherein the first device further comprises a penetrating element that is capable of being advanced radially outwardly from the first device, the direction of advancement of the penetrating element being aligned to a directional signal produced by the directional signal source;

b) inserting, via a percutaneous route, a second device into the second vessel, wherein the second device comprises a sensor, wherein the sensor is capable of detecting a directional signal;

c) generating a directional signal and aligning the first and second devices relative to each other such that penetrating element is advanced radially from the first vessel towards the second vessel, thereby forming a channel enabling fluid communication between the first and second vessels; and d) enlarging the channel to form a fistula.

A second aspect of the invention provides for a method of connecting two adjacent vessels within the body of a patient, said method comprising the steps of:

a) introducing a first source device into a first vessel, the first device comprising at least one signal electrode for generating an asymmetric electric field;

b) introducing a second sensing device into a second vessel, the second device comprising at least one detector for detecting the asymmetric electric field;

c) aligning the first and second device relative to each other based on the electric field generated by the first device that is detected by the detector on the second device;

d) forming a conduit between the first vessel and the second vessel; and e) removing the first and second devices to leave the first and second vessels connected via the conduit.

A third aspect of the invention provides a system for connecting two vessels within the body of a patient, the system comprising:

a) a first source device that is located in a first vessel, the first device comprising at least one signal electrode for generating an asymmetric electric field;

b) a second device located in a second vessel adjacent to the first vessel, the second device comprising at least one detector for detecting the asymmetric electric field; and c) connection apparatus for connecting the two vessels wherein, the connection is directed by aligning the first device with the second device via the asymmetric electric field generated by the first device being detected by the second device, and delivering the connection apparatus along the direction indicated by the alignment.

Optionally the connection apparatus comprises the first source device. Suitably, the at least one signal electrode is located on the connection apparatus. Alternatively, either the first or the second devices comprise the connection apparatus. Typically, the first and/or second devices comprise catheters. Suitably, the first and/or second devices comprise guidewires. In embodiments of the invention where the first device comprises the connection apparatus, the first device is also referred to herein as the 'launching device'. Likewise, where the second device does not comprise the connection means it is, thus, also referred to herein as the 'target device'.

A fourth aspect the invention provides a system for connecting two vessels within the body of a patient, the system comprising:

a) a launching device suitable for location within a first vessel, the launching device comprising (i) an elongate outer sheath with a distal end and a proximal end, the outer sheath defining and enclosing an interior lumen;

(ii) a signal transducer located at the distal end of the outer sheath, the signal transducer being arranged so as to generate an asymmetric electric field; and (iii) a traversing member for traversing the tissue intervening the first and second vessels, the traversing member being movable between a retracted position within the lumen at the distal end of the outer sheath of the launching device, and a deployed position extending outside of the outer sheath of the launching device;

and b) a target device suitable for location within a second vessel, the target device comprising (i) an elongate outer sheath with a distal end and a proximal end, the outer sheath defining and enclosing an interior lumen; and (ii) a detector located at the distal end of the outer sheath;

wherein, in use, the signal transducer on the launching device generates an asymmetric electric field that is capable of being detected by the detector on the target device, and when the signal is detected by the detector on the target device it is determined that the devices are located in the correct alignment within their respective vessels such that the traversing member can be deployed from its retracted position within the launching device to traverse the tissue intervening the first and second vessels and form a connection between the first vessel and the second vessel.

A fifth aspect of the invention provides a system for traversing tissue intervening first and second body cavities comprising:

a) a first source device that is located in a first body cavity, the first device comprising at least one signal electrode for generating an asymmetric electric field;

b) a second device located in a second vessel adjacent to the first body cavity, the second device comprising a detector for detecting the asymmetric electric field generated by the first source device;

c) connection apparatus for connecting the first body cavity and the second body cavity; and d) an electronic alignment monitor unit that is in communication with the first and second devices that is capable of generating the asymmetric electric field in the source device, and detected signal in the target device, and provide a visual or audible display to indicate alignment to the user.

wherein, the connection is directed by aligning the first device with the second device via the asymmetric electric field generated by the first device being detected by the second device, and delivering the connection apparatus along the direction indicated by the alignment.

Optionally, the electronic alignment monitor unit is comprised within a handle that connects to the first device via rotational connectors (commutators). Typically, the connection acts as an arterio-venous fistula to provide vascular access for dialysis. Suitably, the connection creates a radial cephalic fistula, a brachial cephalic fistula, a brachial basilic fistula or a basilic basilic fistula.

A sixth aspect of the invention provides for a percutaneous surgical catheter device comprising:

(a) an elongate body having distal and proximal ends, the body comprising a hollow sheath, which sheath defines a lumen that extends along at least a substantial portion of the body;

(b) a signal transducer located within the distal end of the elongate body, wherein the signal transducer is arranged to generate an asymmetrical electric field;

(c) a penetrating member that is housed slideably within the lumen and is capable of extension out of the distal end of the elongate body;

wherein the direction of extension of the penetrating member is aligned with the asymmetrical electric field.

A seventh aspect of the invention provides for a percutaneous surgical catheter device comprising:
- (a) an elongate body having distal and proximal ends, the body comprising a hollow sheath, which sheath defines a lumen that extends along at least a substantial portion of the body;
- (b) a penetrating member that is housed slideably within the lumen and is capable of extension out of the distal end of the elongate body;
- (c) a signal transducer located within the distal end of the penetrating member, wherein the signal transducer is arranged to generate an asymmetrical electric field;

wherein the direction of extension of the penetrating member is aligned with the asymmetrical electric field.

In an eighth aspect of the invention provides for a penetrating member for use in a percutaneous surgical catheter device, the penetrating member having a proximal and a distal end, wherein at or near the distal end of the penetrating member is located a signal transducer, wherein the signal transducer is arranged to generate an asymmetrical electric field.

In a specific embodiment of the seventh and eighth aspect of the invention, the elongate body comprises an aperture in the side wall in or near to the distal end, thereby allowing extension of the penetrating member in a direction that is substantially radial relative to the longitudinal axis of the elongate body. Suitably, the signal transducer comprises at least two electrodes and is capable of generating an electric field, or optionally at least four signal electrodes. Optionally, the electrodes are switchable to produce fields of varying angular dependence. In a specific embodiment, the electrodes are switchable to produce multipolar (e.g. dipole and/or quadrupole) fields.

Suitably, the signals from transmitted fields of varying angular dependence are combined using an algorithm to produce a composite signal with enhanced angular dependence. In a specific embodiment, the percutaneous surgical catheter device according to the present invention further comprises one or more ring electrodes positioned proximal and/or distal to the signal electrodes to permit longitudinal alignment of the system.

Optionally, the penetrating member comprises a hollow needle. Suitably, the crossing needle is formed of shape memory alloy—such as nitinol—or stainless steel or titanium. Alternatively the penetrating member may comprise a flexible guidewire with an optional sharpened tip. In a specific embodiment, the crossing needle is heated so that it bends as part of its deployment. Alternatively, the hollow needle is formed of one or more sections arranged concentrically within the inner lumen in a telescopic manner.

DRAWINGS

The invention is further illustrated by reference to the accompanying drawings in which:

FIGS. 1a and 1b represent an embodiment of the apparatus of the invention comprising an arterial (source) catheter (FIG. 1a), a venous (sensing) catheter (FIG. 1b), and a handle and a user interface of the device.

FIG. 2a is a more detailed representation of the source catheter according to an embodiment of the present invention.

FIG. 2b is a cross sectional representation of the source catheter of FIG. 2a along the line of BB.

FIG. 2c is an expanded view of the distal end of the source catheter within the circle E in FIG. 2a.

Figure 5A:
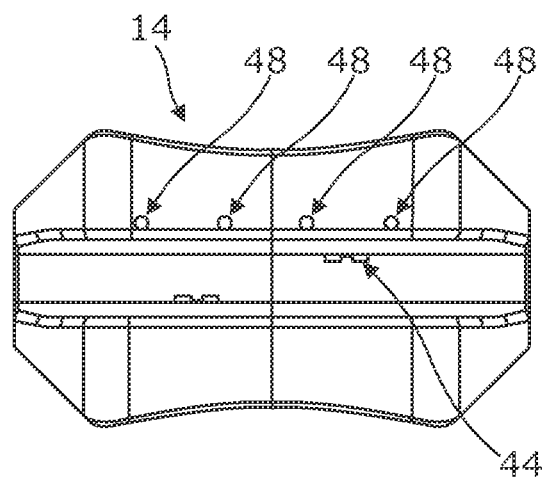
Figure 5B:
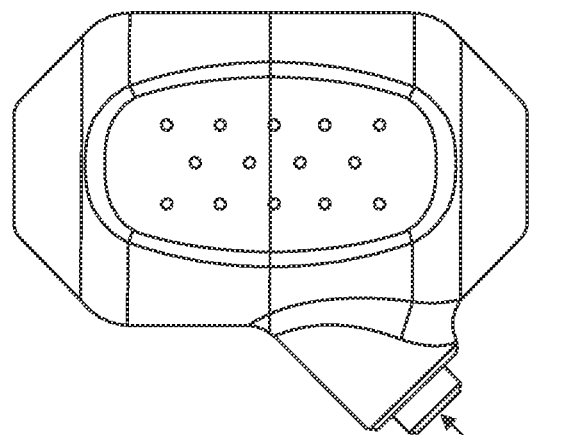
Figure 5C:
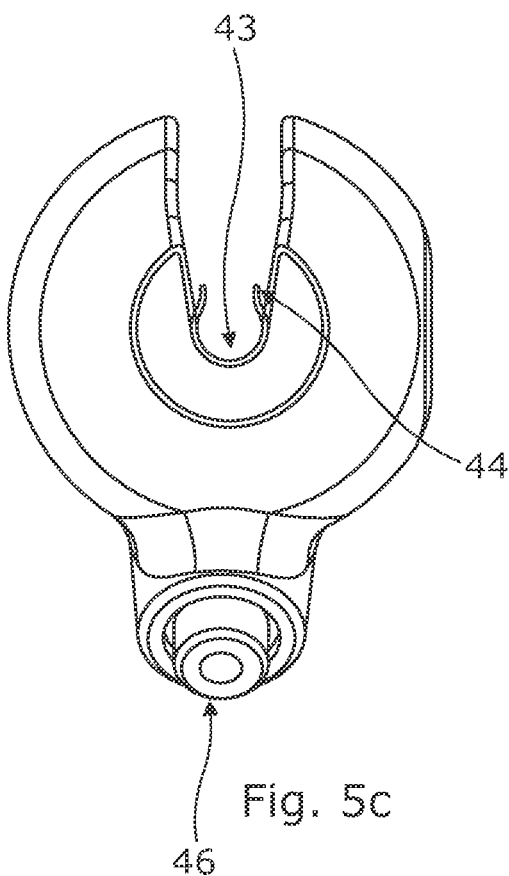

FIGS. 5a-c are detailed representations of a specific embodiment of the system handle and user interface.

Figure 6A:
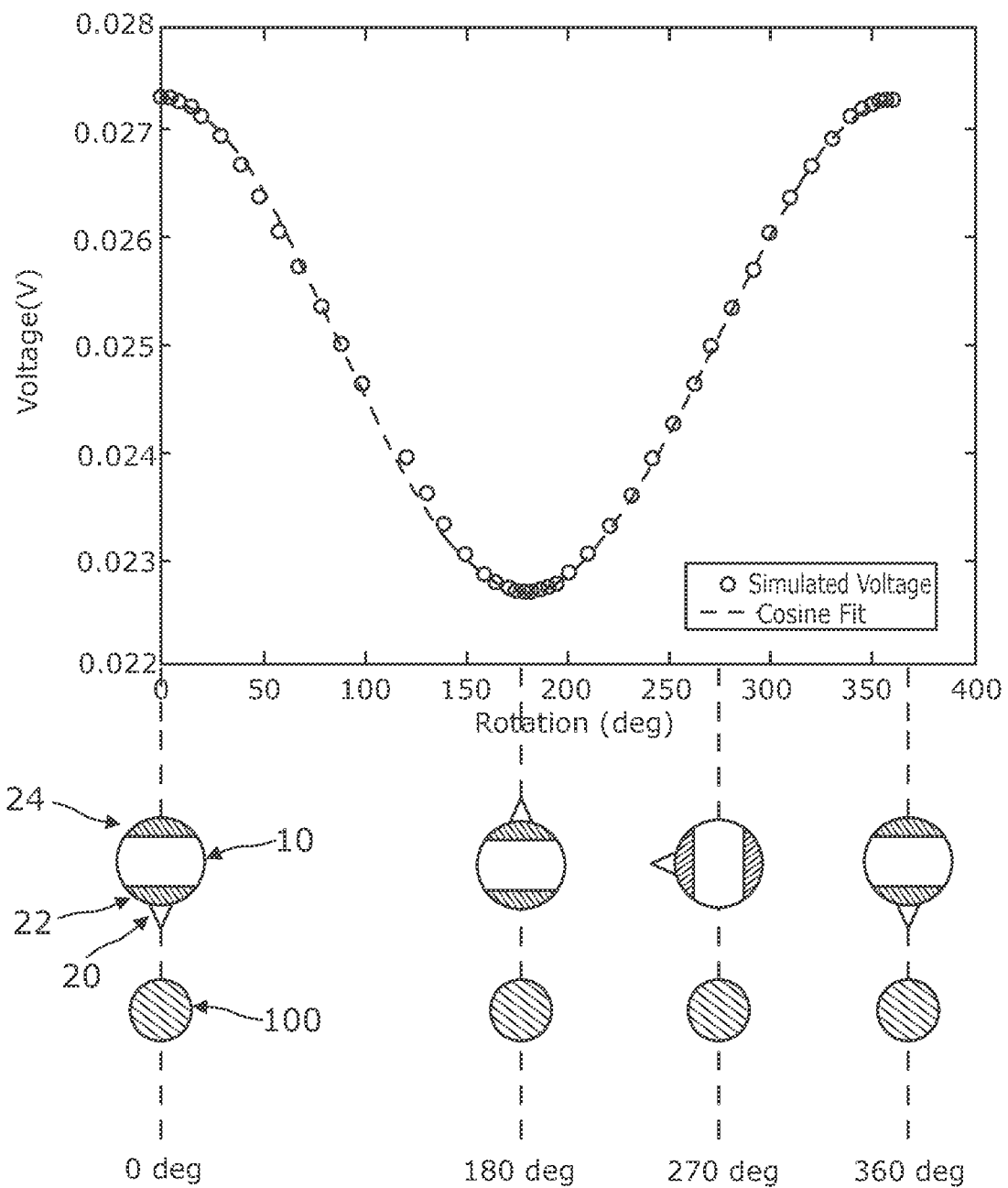

FIG. 6a is a diagram indicating the typical measured field strength versus the rotation of the source catheter relative to the sensing catheter.

Figure 6B:
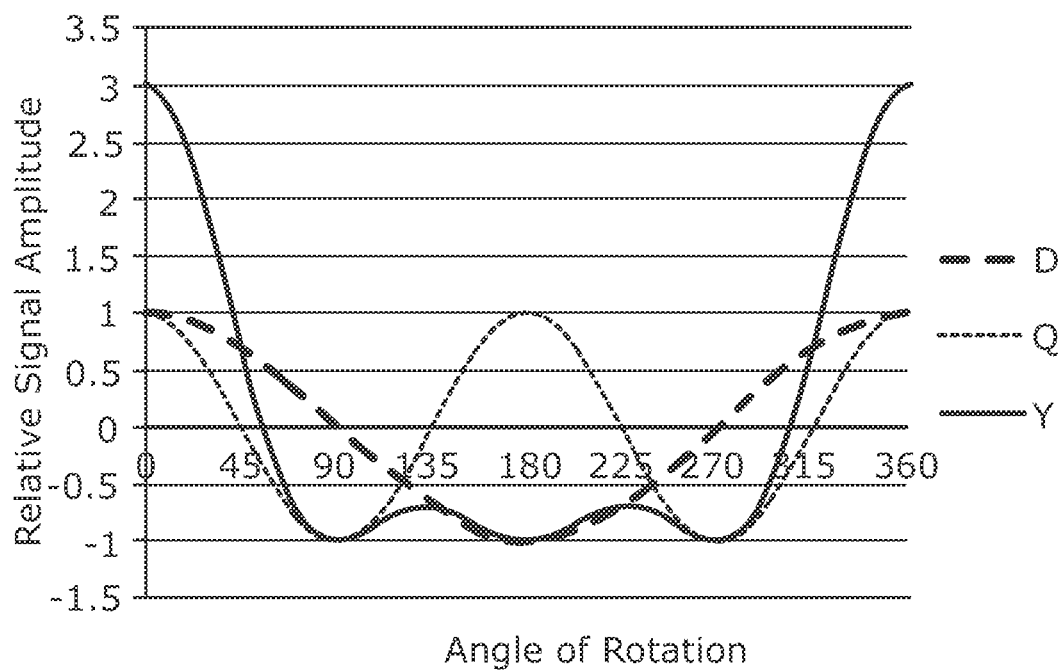

FIG. 6b is a diagram showing the measured field strength vs the rotation for a two element and a four element electrode, and how they combined to give a narrower peak.

Figure 6C:
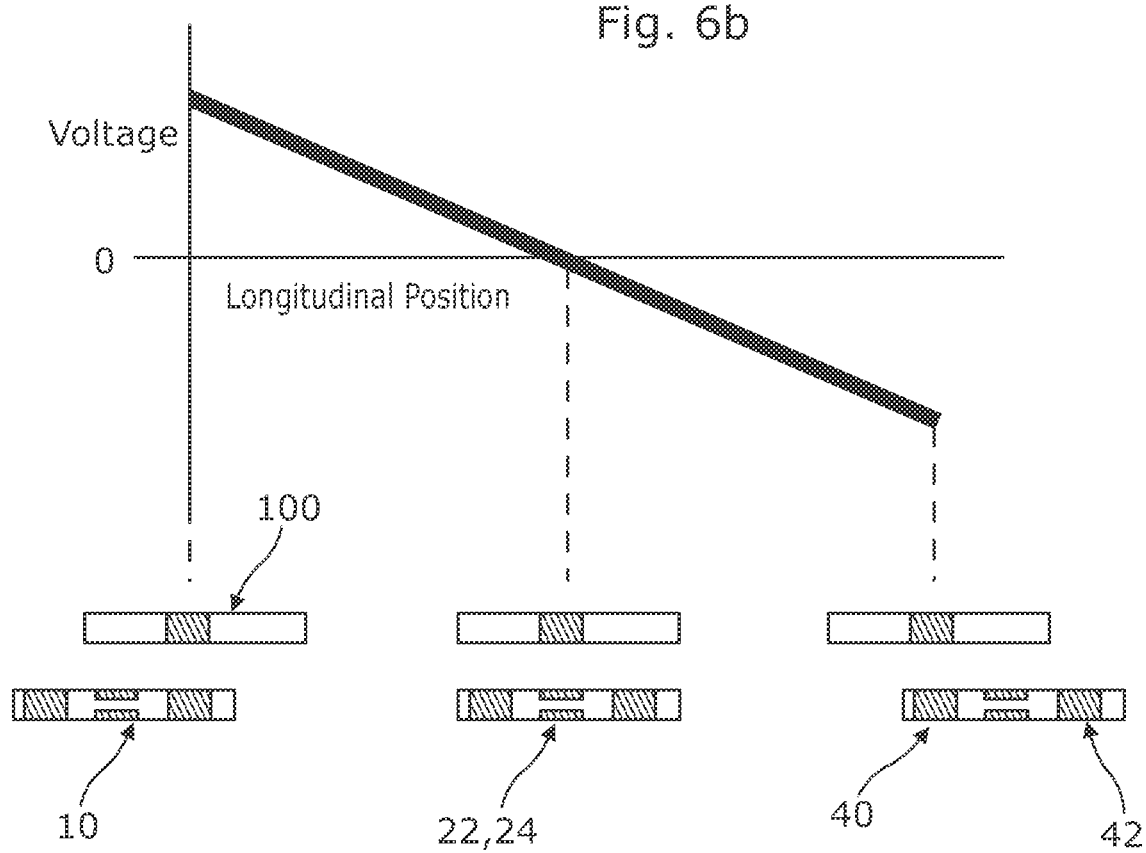

FIG. 6c is a graph showing signal measured from longitudinal alignment electrodes.

Figure 7:
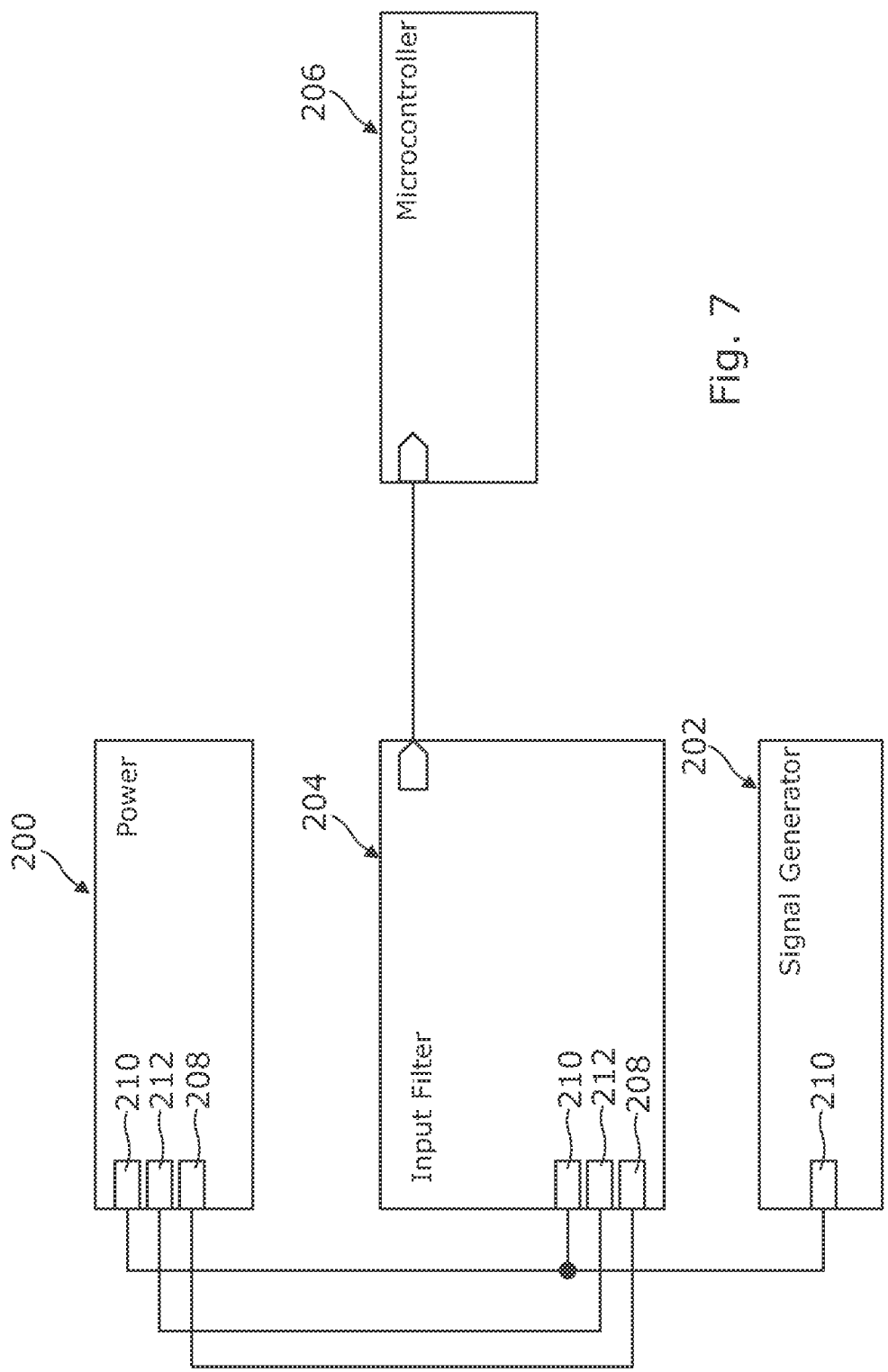

FIG. 7 is a block diagram representation of a specific embodiment of the overall electronic control system for the invention.

FIGS. 8a to f is a chronological step-wise representation of the clinical procedure for using the device to connect two adjoining body vessels—in this embodiment an artery and a vein—with a covered stent graft.

DETAILED DESCRIPTION

All references cited herein are incorporated by reference in their entirety. Unless otherwise defined, all technical and scientific terms used herein have the same meaning as commonly understood by one of ordinary skill in the art to which this invention belongs.

The invention provides for apparatus in the form of medical devices each comprising an elongated shaft assembly, typically in the form of a catheter that comprises functional elements at the distal portion and a user or operator interface at the proximal terminus. The user interface may comprise a handle, handle assembly or hub.

Prior to setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As used herein the terms distal and proximal are used to refer to orientation along the longitudinal axis of the apparatus. Since the devices of the invention are elongate in nature and conform to a single dimension, in use the distal direction refers to the end of the device furthest away from the operator and the proximal direction the end of the device closest to the operator. It should be noted that the term proximal should not be confused with the term 'proximate', which adopts its conventional meaning of 'near to'.

In its broadest configuration the apparatus of the invention comprises an elongate shaft assembly which may engage with or attach to a handle assembly. The elongate shaft is suitably configured for percutaneous use, such as via the intravascular, intra-venous and intra-arterial modes; that involves introduction into a hollow anatomical vessel within the body of a subject animal or patient. The handle assembly remains outside—i.e. external to—the body of the subject. In a specific embodiment of the invention the elongate shaft comprises or consists of a catheter, suitably comprising a tube portion that may define one or more lumens located coaxially within the shaft. The catheter may be adapted for use with an associated guide wire in convention over-the-wire (OTVV) or monorail configurations. In embodiments where the catheter is adapted for use with a guide wire, the catheter may further comprise an additional lumen that is adapted to accommodate a guide wire. Any such guide wire may be pre-located within the subject in order to facilitate placement of the device when in use.

The device of the present invention is suitable for intravascular use. In embodiments of the invention the device may be used within the central vasculature such as the coronary artery and vein as well as in peripheral vasculature such as the blood vessels of the limbs, the head and neck, the groin, or anywhere suitable for the creation of an arteriovenous fistula.

The AVF Surgical Device

According to a specific embodiment, the apparatus of the current invention comprises three main components: a source catheter 10, a sensing catheter 100, and an electronic alignment monitor system 200. According to one embodiment of the invention the source catheter 10 may be located within an artery and the sensing catheter 100 may be located within an adjacent vein, or vice versa.

According to one embodiment of the invention the term "catheter" refers to a device that comprises an elongated shaft. The shaft is typically is provided with a central lumen that extends along its entire length. The elongate shaft of embodiments of the invention are suitably constructed as catheters in a variety of sizes typically ranging from about 0.15 mm up to about 4 mm in diameter (corresponds to French sizes 0.5 to 12). The elongate shaft is suitably constructed from a polymeric material such as a silicone rubber or a polymer including thermoplastic elastomer, PEEK, polyimide, high density polyethylene (HDPE), Pebax, and/or nylon; or composites thereof. All or a portion of the shaft may also comprise a low friction or lubricious coating that may, for example, include a fluoropolymer such as a PTFE or parylene. All or a portion of the shaft may also be reinforced using various arrangement of metallic filaments. All or a portion of the shaft may also be replaced by laser cut metallic tubing such as nickel titanium alloy, stainless steel, or other biocompatible metal alloys.

A central lumen 38 provides a conduit which may allow engagement with a pre-located guide wire. The central lumen 38 may extend entirely along the shaft such that the within or adjacent to the distal terminus there is comprised an aperture allowing fluid communication between the central lumen and the hollow anatomical structure within which the shaft is located. In an embodiment of the invention, the central lumen is formed from a polymer liner that sits coaxially within the elongate shaft. Suitably the polymer liner is comprised of a material such as a fluoropolymer, for example PTFE. In an embodiment of the invention the distal portion, at least, of the polymer liner may be linked or otherwise fixed to the distal part of the elongate shaft and the main portion of the polymer liner is allowed to move freely within and with respect to the elongate shaft. Embodiments of the invention permit for location of the central lumen centrally within the body of the elongate shaft or at a position that is radially offset from the central longitudinal axis FIG. 1a shows an embodiment of a source catheter 10 according to the present invention. The source catheter 10 comprises an elongate body 12 having a proximal and distal end. Toward the proximal end of the body 12 is positioned a first Luer connector 14 in communication with the body 12; and a second Luer connector 16 in communication with the lumen of the penetrating member 20.

The source catheter 10 further comprises a guide wire 18 that is operable between a retracted position wherein the guide wire 18 is retained within the lumen, and an extended position wherein the guide wire 18 extends outwardly from the distal end of the lumen, and a penetrating member 20. The guide wire 18 runs co-axially within the penetrating member 20 for the entire length of the catheter 10. The penetrating member 20 is constrained inside the catheter 10 to lie along the axis of the catheter 10. The penetrating member 20 has a pre-formed curve at its distal end, so that when it exits the catheter 10 it adopts a shape that curves in a radial direction with respect to the axis of the catheter 10. In the embodiment shown in FIG. 1a, the penetrating member 20 is ejected through an opening or aperture 19 in the side wall of the catheter 10. The aperture 19 may be covered with a sliding cover 21 such as a tube or sleeve (not shown) that can be withdrawn when the penetrating member 20 is ejected. Furthermore, only when the guide wire 18 is in the retracted position can the penetrating member 20 be ejected from the catheter 10.

The penetrating member 20 may be a retractable hollow needle or stylet formed from a suitable material including polyether ether ketone (PEEK), carbon fibre loaded liquid crystalline polymer, tungsten carbide polyimide, stainless steel, gold, platinum, shape memory alloy (including NiTinol) or other suitable surgically compatible metal alloys. Typically, the penetrating member is formed from a radiopaque material so as to facilitate visualisation during surgical procedures when using X-ray guidance. The penetrating member 20 may further comprise one or more echogenic surfaces to further facilitate use with ultrasound visualisation (e.g. IVUS, phased array) technologies. The penetrating member 20 is provided with a sharp tip at its distal end, which is used to puncture and penetrate tissue at the site of treatment. The lumen of the penetrating member 20 allows the delivery of a standard guide wire 18 from one vessel to another. The lumen of the penetrating member also allows for administration of substances, including and pharmaceutical compositions and contrast medium, to the site of treatment through the lumen of the penetrating member 20 if required. The lumen of the penetrating member 20 may also be used as an aspiration channel to extract fluids from the site of treatment and/or to take a tissue biopsy.

Toward the distal end of the body 12 there are positioned a pair of electrodes 22, 24 spatially separated around the circumference of the body 12 such that they are substantially diametrically opposed. In one embodiment of the invention, the pair of electrodes 22, 24 are arranged along an axis that is substantially aligned with the direction of deployment of the penetrating member when it is extended outwardly from the source catheter. As best seen in FIG. 2*a*, electrode wires 26, 28 (not shown) extend proximally from the electrodes along the lumen until they connect with pads 34 and 36 on the rigid clip-on section 32.

In the embodiment of the invention shown in FIGS. 1*a* to 1*c*, a handle 30 provides a first user interface with the catheter 10. The handle 30 is removably attached to the body 12 via the rigid clip-on section. The handle 30 is arranged on the body 12 so as not to interfere with insertion of the catheter 10 into the body, suitably the handle 30 is positioned toward the proximal end of the body 12.

FIG. 1*b* shows an embodiment of a sensing catheter 100 according to the present invention. The sensing catheter 100 comprises an elongate lumen 102 having a proximal and distal end. Toward the proximal end of the lumen 102 is positioned a Luer connector 104.

The sensing catheter 100 comprises a hollow guide wire 106 and two ring electrodes 108, 110. Electrode wires 112, 114, each of which is connected to a respective ring electrode, extend proximally in the interior of the lumen 102 and exit the lumen at the proximal end through the Luer connector 104.

Having described the main features of the apparatus comprising the source catheter 10 and sensing catheter 100, a detailed description of the features presented will now be provided with reference to FIGS. 2*a-d*, 3*a-b*, and 4*a-c*.

As shown in FIG. 2*a*, the source catheter 10 comprises several elongated tubes that are coaxially aligned and have overall a proximal and distal end. FIGS. 2*a-c* show the features of the source catheter 10 in more detail.

FIG. 2*a* shows the source catheter 10 in side view with the handle 30 removed. On the body of the catheter 10 there is a rigid clip on section 32 of a larger diameter than the body 12 which comprises two ring electrodes 34, 36. This section is formed so as to mate with the handle 30 and allow for free rotation of the handle through a 360 degree electrical connection.

The first Luer connector 14 allows for the manipulation of source catheter 10 and the second Luer connector 16 allows for the manipulation of a penetrating member 20 such as a needle while stopping blood from exiting. The penetrating member 20 and Luer connector 16 also allow for a syringe to be connected and facilitate the insertion of therapeutic agents, for example, contrast medium.

In one embodiment of the catheter 10 the two electrodes 22, 24 are diametrically opposed each occupying less than half of the circumference of the body 12. In an embodiment of the invention, one electrode 22 serves as the positive electrode, and the second 24 serves as a negative electrode, thereby forming a dipole configuration. Several other arrangements are also possible, such as an evenly spaced array of more than two electrodes arranged around the circumference of the body 12, embodiments of this type would suitably include quadrupole or octupole configurations of electrodes. The electrodes 22, 24 are located distally to the penetrating member 20 along the body of the source catheter 10 in order to be aligned with the end of the penetrating member 20 when ejected. This ensures that point which the penetrating member 20 punctures into the vein corresponds to and is aligned with the position of peak field strength generated by the electrodes. In an alternative embodiment the electrodes 22, 24 can be located proximal to the penetrating member 20.

A cross section along BB of a source catheter 10 according to an embodiment of the invention is shown in FIG. 2*b*. The catheter 10 comprises a coaxial arrangement of an outer sheath 35 that surrounds and thereby defines an inner lumen 38. Located within the lumen 38 is an inner sheath 37. The inner sheath 37 is connected to the outer sheath 35 using adhesive throughout the whole length of the catheter 10. The electrode wires 26, 28 are also located within the lumen 38 and pass in an axial direction along the lumen 38 to the proximal end of the device. The inner sheath 37 and outer sheath 35 may be formed of any material that can prevent the ingress of water and other bodily fluids such that the lumen 38 is substantially waterproof. This protects any electrical signal passing through the electrode wires 26, 28 from shorting. In an alternative embodiment, the outer sheath 35 and inner sheath 37 are replaced by one sheath. In this embodiment, the electrode wires are embedded directly within the single sheath.

The inner sheath 37, when present, defines an inner lumen within which is positioned the penetrating member 20, such as a needle, and optionally a guide wire 18. In order to facilitate use of the catheter 10, the guide wire 18 may be located coaxially within the hollow core of the penetrating member 20. In this way the penetrating member 20 is prevented from extending outside the body 12 while the guide wire 18 is in position. Only when the catheter 10 is aligned and the guide wire 18 is removed can the penetrating member 20 be advanced from the opening 19 in the side wall of the catheter body 12. This embodiment of the invention avoids the need for a preformed needle to be inserted during the procedure and risk disrupting the alignment. This arrangement also removes the need for a separate guide wire lumen. Alternatively, if the operator prefers to use a guide wire of greater diameter than that permitted by the size of the needle—particularly in smaller devices that are intended for paediatric use—the guide wire 18 may sit within the inner lumen and be removed and replaced with the penetrating member 20 at the appropriate point during the procedure. Furthermore, in an alternative embodiment the guide wire 18 may be arranged in an external monorail configuration and sliding cover or sheath 21 may be used to prevent the penetrating member 20 from exiting the lumen.

Electrode wires 26, 28 provide electrical connection from each electrode 22, 24 to a respective ring electrodes 34, 36 in the rigid clip on section 32 positioned towards the proximal end of the catheter 10. In this embodiment the ring electrodes 34, 36 form a convenient rotary connection with the handle 30 when attached to the rigid clip on section 32 thereby preserving electrical connection between the handle 30 and the source catheter 10 through any degree of rotation about the axis of the catheter 10. Other embodiments using an electrical plug or conventional hub are also suitable.

An expanded view of the distal end of the source catheter 10 is shown in FIG. 2*c*. The typical spatial arrangement of the two electrodes 22, 24 is shown. In this embodiment, the electrodes 22, 24 are aligned and diametrically opposed on either side of the catheter body 12. In another embodiment the electrode, or each pair of electrodes, are diametrically opposed but not aligned, with one electrode axially offset from the other electrode along the body 12. Through the opening 19 the arrangement of the guide wire 18 passing through the penetrating member 20 is also visible demonstrating how the guide wire is able to lock the penetrating member 20 in place prior to withdrawal of the guide wire 18 and deployment of the penetrating member 20.

In an embodiment of the source catheter 10 (not shown) the penetrating member 20 may be a straight tube made of a shape memory alloy, with an insulated conducting wire installed into the lumen. The distal end of the wire will have the insulation removed, so that an electrical circuit is formed from the proximal end of the wire to its distal end, via an electrical contact with the distal end of the penetrating member, and then from the distal end of the penetrating member to its proximal end. If electrical contact is then made to the proximal end of both the tubular penetrating member and the central wire a pulsed electrical current is passed through the circuit. This will heat the penetrating member above its transition temperature and deform the member to adopt a preset curved shape that will then cross from one vessel to another. Changing the mark-space ratio of the current waveform can generate a proportional control of the deformation.

Figure 2D:
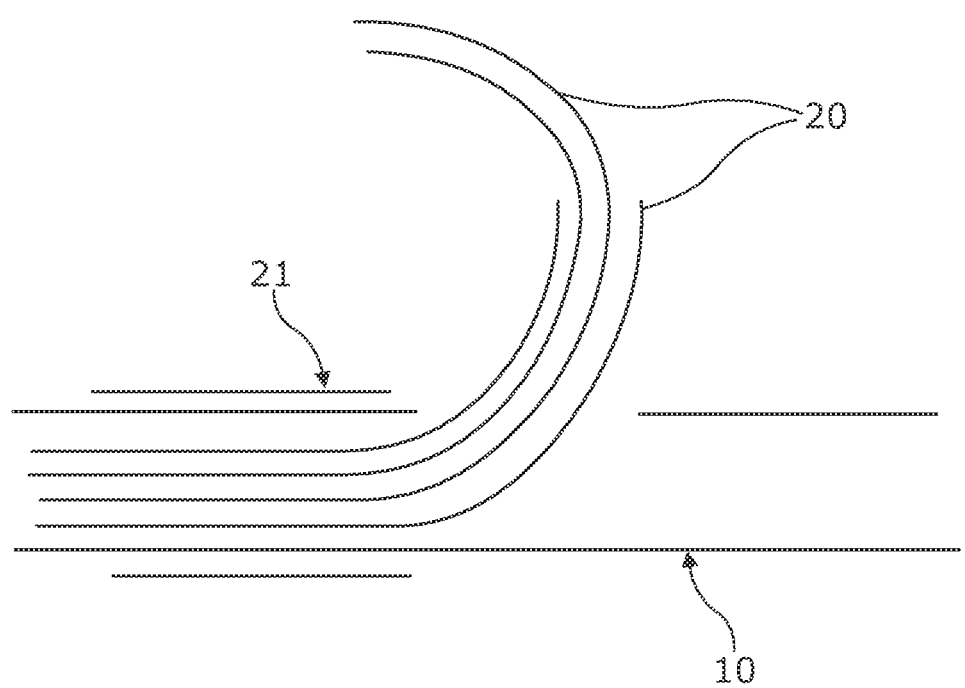
FIG. 2d is a sectional view of an embodiment of a penetration member of the source catheter comprising two hollow pre-curved needles.

As shown in FIG. 2d, the penetrating member 20 of another embodiment of the source catheter 10 is shown consisting of two hollow needles arranged concentrically within the inner lumen. Each needle has a pre-defined curvature. The needles are deployed one after the other in a telescopic manner, so that the penetrating member 20 has an increased length and angular curvature.

In an embodiment of the invention one or more further electrodes are mounted on the distal end of the penetrating member 20. In this embodiment the entire penetrating member is insulated except for a section of the distal end that forms an electrical connection to the penetrating member 20 at its proximal end. The one or more further electrodes are not activated when the penetrating member is retracted and only become active when the penetrating member has exited the catheter. Once activated, these one or more further electrodes form an asymmetric electric field. This allows for fine adjustment of the alignment of the penetrating member as it is crossing from the artery to the vein to ensure that it remains on target. Furthermore, in this configuration, the sensing catheter 100 will detect when the penetrating member has successfully penetrated into the vein based on several different measurements including amplitude and conductance.

Figure 3A:
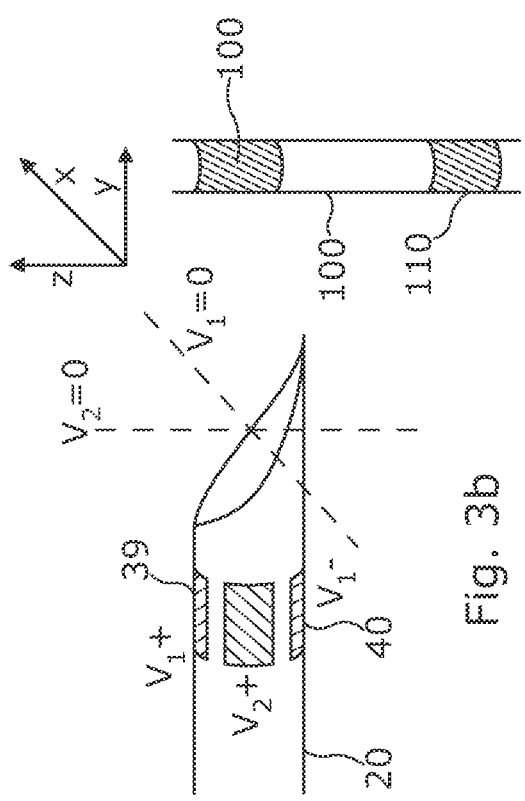
FIG. 3a is a representation of an embodiment of the apparatus of the invention with signal source electrodes arranged on the penetration member, and the sensing catheter.

In FIG. 3a a penetrating member 20 is shown that has a positive ring electrode 39 and a negative ring electrode 41 on its distal tip. The electrodes 39, 41 together generate a directional electric field. The sensing electrodes 108, 110 on the sensing catheter 100 measures the dipole electric field created by the two source electrodes 39, 41. As the penetrating member 20 approaches the sensing catheter 100 the measured signal will reach a maximum when the tip of the penetrating member 20 is nearest the sensing electrode 100. If the penetrating member 20 advances beyond (i.e. overshoots) the sensing catheter 100 the signal will start to decrease. As an alternative, the sensing electrodes 108, 110 can be located on the penetrating member 20 and the source electrodes 39, 41 are on the sensing catheter 100. This functionality can be accomplished electronically or using software to configure the apparatus accordingly.

Figure 3E:
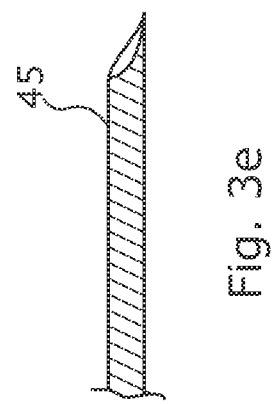
FIG. 3e is a representation of an embodiment of the apparatus of the invention with a single source electrode comprising of the entire length of the penetrating member.
Figure 3D:
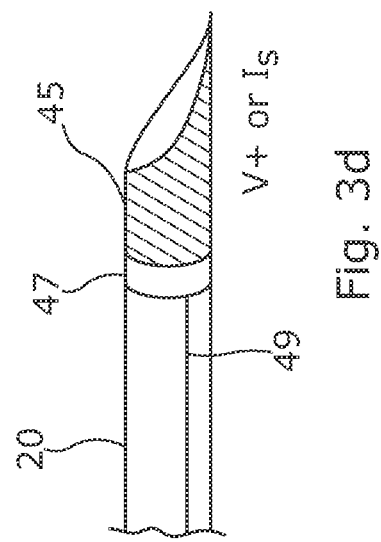
FIG. 3d is a representation of an embodiment of the apparatus of the invention with a single source electrode forming the tip of the penetrating member
Figure 3C:
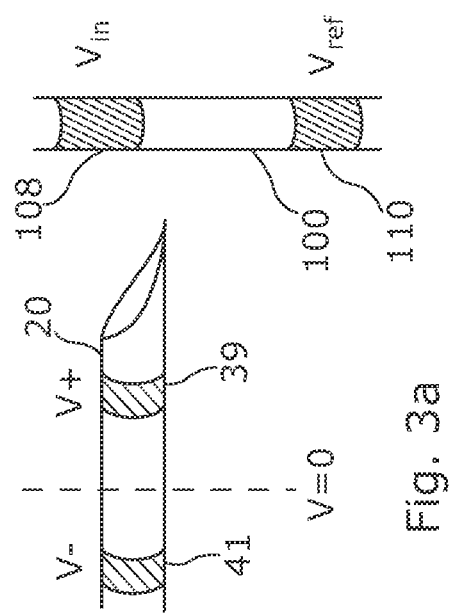
FIG. 3c shows a cross-sectional view of the penetrating member shown in FIG. 3b.
Figure 3B:
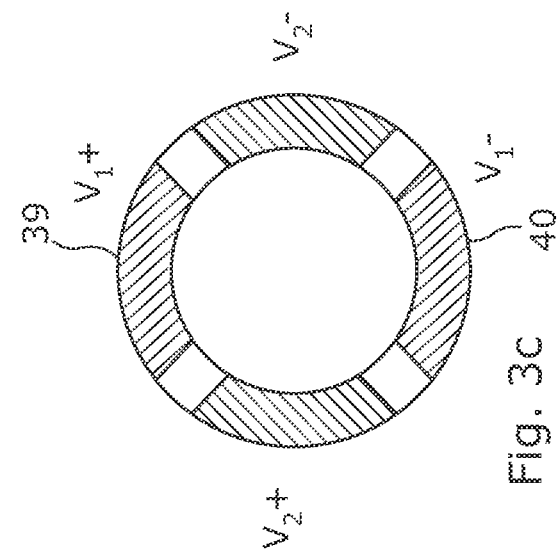
FIG. 3b is a representation of an embodiment of the apparatus of the invention with two pairs of signal source electrodes arranged on the penetration member in a diametrically opposed fashion, and the sensing catheter

FIG. 3b shows an alternative embodiment of the penetrating member 20 having two pairs of source electrodes 39, 41 on its distal end. Each pair of source electrodes 39, 41 are arranged in a diametrically opposed fashion on a circumference of the penetrating member 20; the first pair of electrodes 39, 41 angularly displaced by approximately 90° from the other pair of electrodes. This is best shown in FIG. 3c which is a cross-sectional view of the penetration member 20 at the position of the electrode pairs.

Each pair of electrodes creates a dipole electric field with a zero value along a plane that lies equidistant between them when the electrodes are activated. In this arrangement the signal measured by the electrodes 108, 110 on the sensing catheter 100 will vary with movement of the penetrating member 20 in the x-y plane (i.e. along or across the longitudinal axis L of the sensing catheter 100; as shown in FIG. 3c). A measured value of OV when both pairs of electrodes are active indicates that the penetrating member 20 is aligned with the positive sensing catheter electrode 108. A value greater than OV indicates a degree of misalignment. The amplitude of signal is indicative of alignment with values closer to null (OV) indicating greater alignment.

This embodiment need not be limited to having two pairs of electrodes. Similar functionality may be achieved with three or more pairs of electrodes, for example, 4 pairs or 8 pairs (i.e. quadropole or octopole), or more pairs of electrodes on the penetration member 20.

FIG. 3d shows another embodiment of a penetrating member 20 having one or more electrodes. In this embodiment, the penetrating member 20 has a single ring source electrode 45 that forms the tip of the penetrating member 20. When the penetrating member is formed of a conducting material, such as metal, this configuration requires insulating material 47 to separate the electrode 45 that forms the tip of the penetration member 20 and the remainder of the penetration member 20. A wire 49 connects the electrode 45 to a power source. In use, current is applied to the source electrode 45 and a voltage is measured on the sensing electrode 108 relative to the ground signal measured from the grounding electrode 110 on the sensing catheter 100. In an alternative embodiment the electrode 45 acts as voltage source and the current is measured at electrode 108. The current or voltage measured by the electrode 108 on the sensing catheter 100 will increase when the tip of the penetrating member 20 is nearest the sensing electrode 108 and will be at a maximum if the penetrating member 20 contacts the sensing electrode 108. A high or maximum signal may be used to indicate that the penetrating member has successfully entered the vessel. FIG. 3e shows an alternative embodiment where the entire penetrating member 20 acts as the source electrode 45 and functions as described above.

In a further embodiment of the invention, a penetration member 20 with electrodes 39, 41 or 45 on its distal end form part of a catheter that does not itself comprise radial alignment electrodes. In this embodiment, the electrodes on the penetration member 20 may be used for radial alignment prior to deployment of the penetration member 20. Alternatively, there may be no radial alignment of the catheter prior to deployment of the penetration member 20. In this embodiment, the direction of the penetration member 20 is monitored by the signal generated in the sensing catheter 100 by the electric field created by electrodes 39, 41 or 45 on the penetration member 20.

Figures 4A, 4B:
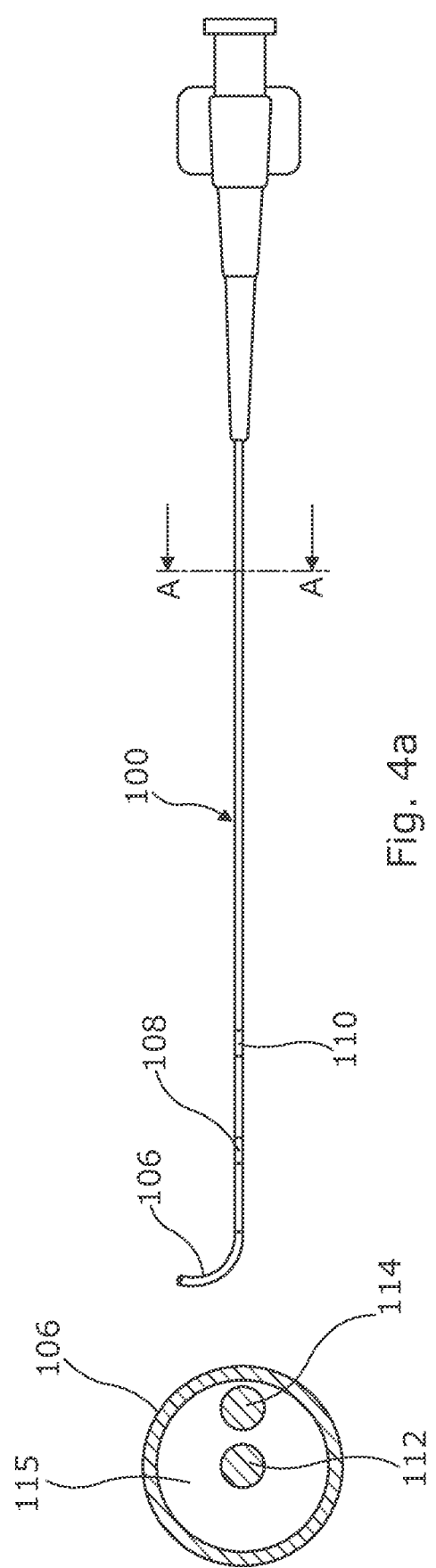
FIG. 4a is a representation of a specific embodiment of the sensing catheter according to an embodiment of the present invention.
FIG. 4b is a cross sectional representation of the sensing catheter of FIG. 4a along the line of AA.

The sensing catheter 100 is shown in more detail in FIG. 4a. The hollow guide wire 106 comprises two ring electrodes 108, 110. In the embodiment shown in FIG. 1b, the most distal electrode is the sensing electrode 108, whilst the proximal electrode is a grounding electrode 110. At the proximal end of the catheter 100 an electrical plug 116 (not shown) is connected to the electrode wires 112, 114 (not shown) that run along the length of the sensing catheter 100 within a central lumen. Each of the electrode wires 112, 114 is in electrical connection with a respective ring electrode 108, 110. Suitably, the connector may comprise any connector suitable for transmitting an electrical signal, in one embodiment, the connector is a male auxiliary plug.

FIG. 4b shows a cross section of the lumen 102 along AA as shown in FIG. 4a. The electrode wires 112, 114 are shown located within the lumen 115 of the body 106. In embodiments of the invention the body 106 may be comprised within a guide wire, both hollow or not, or similar catheter of small diameter.

The apparatus comprising the two catheters 10, 100 are connected to an electronic alignment monitor system 200. The electronic alignment monitor system 200 applies a voltage to the distal electrodes 22, 24 of the source catheter 10. In one embodiment voltage is applied to spatially opposite electrodes. The voltage applied is preferably an AC voltage. Suitably, the voltage may alternate with a frequency of between 10 Hz and 1 MHz, more suitably the voltage may alternate at a frequency of between 1 kHz and 100 kHz. Typically, the amplitude of the voltage may be between 1 mV to 10 V. Suitably, the current has to be within the limits set by EN60601-1. The electronic alignment system 200 may also display the alignment signal.

In one embodiment of the invention, the electronic alignment monitor system 200 is comprised within a hand-held unit which serves as the handle 30 for the source catheter 10 as shown in FIGS. 5a and 5c. The handle 30 has a groove 43 into which the handle engagement, or rigid clip-on section 32 of the source catheter 10 clips. Pads 44 in the handle 30 brush against the ring electrodes 34, 36 creating a 360 degree rotatable electrical connection to the source electrodes 22, 24 at the distal end of the catheter 10 via electrode wires 26, 28. The handle 30 is also in electrical communication with the sensing catheter 100. Suitably, the connection is via a female auxiliary jack plug 46 although any suitable means of hard-wired or wireless connection is encompassed within the scope of the invention. The female auxiliary jack plug connector 46 that links the sensing catheter 100 to the handle 30 on the source catheter 10 also functions as an on off switch for the whole system, turning it on when plugged in and indicating to the operating clinician that they need to progress to the next step.

The integrated alignment system 200 within the handle 30 displays alignment data using a visual display 48. The visual display provides feedback to the operator of the relative positioning of the source catheter 10 and the sensing catheter 100, and particularly whether the catheters 10, 100 are correctly aligned with each other in order to undertake the creation of a fistula successfully. For example, in the embodiment shown in FIGS. 5a to c, as the source catheter is rotated and reaches alignment the read-out successively illuminates a series of the LED's. In this embodiment, the LED's may also indicate other important information, including, but not limited to, when the battery is close to being discharged (flashing red), or flashing green when the system needs to be calibrated. Various alternative forms of user displays may also be contemplated for inclusion on the handle 30 or on a display screen or device remote from the handle. By way of non-limiting example, displays may be visual, such as by illuminating one or a series of LED's, or via an LED/LCD display; aural, such as by combining two intermittent tones (beeps) until a single continuous tone is heard; or via a sensation, whereby correct alignment is indicated to the operator via a vibration of the handle; or a combination of all or some of these readouts.

The electronic alignment monitor system 200 may be powered by any means. Suitably, the electronic alignment monitor system 200 is battery powered and the batteries are completely integrated into the handle. The system 200 generates an electrical signal that drives the source electrodes 22, 24 on the source catheter 10 as well as processing the signal measured from the sensing catheter 100. The system 200 is also responsible for displaying information to the user, for example by means of the 4 LED's as shown in FIG. 5a. It will be understood that additional or fewer LED's may be used.

The alignment of the catheters 10, 100 for the formation of an AVF is based on the measurement by the sensing catheter 100 of an asymmetrical electric field generated by the source catheter 10. As shown in FIG. 6, an electric potential field measured by the sensing electrode 108 will be greatest when the positive electrode 22 on the source catheter is perfectly aligned with the center of the sensing electrode 108. The minimum voltage measurement will occur when the negative electrode 24 is aligned with the center of the sensing electrode 108. The sensing electrode 108 is in the form of a ring, so its measurements are independent of any rotation of the sensing catheter 100. In essence, the sensing electrode 108 is an omni-directional receiver of the electrical signal (or absence of signal) generated by the source catheter 10. Therefore, if the opening 19 is in line with the positive source electrode 22 it is possible to align its trajectory with the target vein that it needs to pierce by rotating the source catheter 10 until the peak voltage is detected by the sensing electrode 108. Alternatively the minimum or null signal can be used for alignment. In addition to the active alignment, the electrodes themselves can act as visual indicators under fluoroscopy. This provides the operating clinician with visual confirmation that the source catheter is being rotated properly within the vessel. The measured voltage varies according to a sinusoidal function over 360 degrees with peaks occurring at 0 and 360 degrees, such as when the positive electrode 22 is aligned with the sensing catheter 100. In one embodiment, the user is required to rotate the source catheter 360 degrees once it is in position in order to calibrate the system. This allows the system to record the maximum amplitude in that position. During normal use, the measured signal is compared against the recorded maximum and the degree of alignment is calculated.

In a further embodiment a quadrupole arrangement of electrodes can be used. In this arrangement, when the electrodes are driven with alternating polarity the electric potential field measured by the sensing electrode 100 will vary according to a sinusoidal function over 360 degrees with peaks occurring when one of the positive electrodes is aligned with the sensing catheter 100 as shown in curve Q of FIG. 6c. The connection between the electrodes and the AC voltage source can be individually switched so that the same quadruple electrode arrangement can be driven so that two neighbouring electrodes are connected together to a positive voltage, and the other two neighbouring electrodes are connected to a negative voltage, turning the quadrupole electrodes into a dipole arrangement. A combination of the signal obtained with the quadrupole configuration, $Q(\theta)$ and dipole configuration $D(\theta)$ can be obtained by repeatedly switching between the two configurations. FIG. 6c shows one example of a combination, where the combination: $Y(\theta)=D(\theta) \cdot Q(\theta)+D(\theta)+Q(\theta)$ has a narrow peak at 0 degrees. This approach gives a narrower peak to increase the accuracy of the alignment.

In a further embodiment of the system a rotary encoder is used in conjunction with the dipole or multi-pole electrode configuration for alignment. This rotary encoder would be housed in the handle and measure the angular position of the source catheter using optical, magnetic, capacitive or mechanical methods. The angular position, in conjunction with the measured signal strength can be used to determine the position of the source catheter relative to the sensing catheter at any time without the need for calibration (for example, an initial 360 degree rotation). After even a slight rotation is it possible to determine its exact position by inferring from the few data points the precise amplitude curve since it is known that it is sinusoidal in shape. Therefore, angular position which corresponds to the peak amplitude can be determined mathematically and the necessary angular rotation of the source catheter to reach alignment can be calculated. The user is then guided using the interface to rotate the catheter the appropriate amount and in the appropriate direction in order to reach alignment.

In a further embodiment of the system another dipole pair of electrodes is placed on the source catheter 10 in order to guide the longitudinal alignment of the catheters 10, 100. These longitudinal alignment electrodes 40, 42 are ring electrodes with the positive electrode (Vcc) 42 placed proximal of the angular alignment electrodes 22, 24 and the negative electrode (-Vcc) 40 placed distal of the angular alignment electrodes 22, 24. Both the positive and negative electrodes 40, 42 are equidistant from angular alignment electrodes 22, 24 and the separation between them may be between 5 mm and 10 cm. The longitudinal alignment electrode pair 40, 42 generates a dipole electric field in the same manner as the angular alignment electrodes 22, 24 and the field is measured by the same sensing electrodes 108, 110 on the sensing catheter 100. Since the field generated is centered on the angular alignment electrodes 22, 24, the amplitude measured by the sensing electrodes 108, 110 when the angular alignment electrodes are aligned is null (FIG. 6b). During longitudinal alignment the system only activates the longitudinal alignment electrodes 40, 42 and during rotational alignment the system activates only the angular alignment electrode pair 22, 24. Alternatively, the system can activate both pairs of electrodes at the same time using different carrier frequencies or rapidly switch between each electrode pair in order to get both measurements at the same time. This approach eliminates or minimizes the need for fluoroscopy to be used during the procedure.

In an embodiment of the invention, the control system 200 has four main sub-blocks: the power unit 201, the signal generator 202, the signal processing unit 204, and the microcontroller unit (MCU) 206. The overall structure is shown in FIG. 7 The power unit 201 is responsible for providing power to the entire system. It consists of three main parts, the batteries 208, a 3 V low drop out (LDO) regulator 210 that provides Vcc, and a 1.5 V LDO regulator 212 that provides the Vcc/2 rail. The signal generator unit 202 is responsible for generating the AC signal which drives the source electrodes 22, 24. A system suitable for generating an appropriate alternating current signal is considered to be within the scope of the invention. Suitably, according to embodiments of the invention the overall design may be based on a diode regulated Wien bridge oscillator, a clock signal from the microcontroller (MCU) or a crystal oscillator. Typically, the system comprises a diode regulated Wien bridge oscillator. The Wien bridge oscillator uses an LMV741 Texas Instruments operational (OP) amplifier which has very low noise (6.5 nV/√Hz) and suitably low supply current (500 µA) and is capable of driving high capacitance loads. This is necessary since it is the last stage before a capacitor AC couples the output to the positive electrode 22 on the source catheter 10. The signal-processing unit 204 handles the raw signal from the sensing electrode 108 in three stages and outputs a DC value to the MCU 206. The purpose of the MCU 206 is to represent the difference in amplitude between the sensing electrode 108 and the grounding electrode 110. The differential signal is first passed through active high pass filters, then an instrumentation amplifier and finally a peak detecting circuit. The microcontroller unit consists of an ATTiny45 and is responsible for the analog to digital conversion and analysis of the magnitude signal received from the signal processing unit 204. It determines the catheter alignment and displays the information to the user, for example, through the LED interface on the handle 30. In alternative configurations some or all of the electronic components within these sub-blocks may be replaced by suitable alternatives as known to those skilled in the art. Furthermore, additional sub-blocks may be added to improve measurement performance, signal processing, or to reduce power consumption. These additional sub-blocks may also enable the use of any of the aforementioned additional features (multipole electrode configurations, rotational encoders, etc.).

In other embodiments of the invention, the alignment of the first and second devices may be by means other than detection of an asymmetrical electrical field. In such embodiments a signal source, such as a transducer or transmitter, is located on the source catheter 10. The signal transducer provides a signal that is directed outwards from the source catheter. Typically, the signal is directed radially outward from the source catheter 10 in a direction that is perpendicular to the longitudinal axis of the source catheter 10. In alternative embodiments of the invention the direction of the signal need not be perpendicular and can be directed at an angle of between 20° and 90°, suitably around 45°, to that of the axis of the source catheter 10. The signal transducer is, thus, comprised within a signal generating means of the apparatus of the invention.

The signal transducer is connected to a signal transmitter (not shown). The signal transmitted can be suitably selected from ultrasound or appropriate electromagnetic sources such as a laser, microwave radiation or via radio waves. In a specific embodiment of the invention the signal transmitter generates an ultrasound signal, which is relayed to the signal transducer, which in turn directs the signal into the surrounding tissue and which may be detected by a sensor located on the second device in order to facilitate correct rotational and/or longitudinal alignment.

Methods of Using the AVF Surgical Device

The method of the invention comprises three main phases of therapy: an insertion phase, a therapy phase and a removal phase. The insertion phase includes the intravascular insertion of the devices and the location of the devices to the site of treatment, in adjacent vessels, where therapy is to be administered. The therapy phase includes alignment of the devices relative to each other followed by formation of a fistula between the respective vessels. The removal phase includes the withdrawal of the devices from the site of treatment; usually back along the initial insertion route. It will be appreciated that the therapy phase may be repeated several times before the removal phase commences.

In a typical embodiment of the invention, after alignment of the devices and formation of a conduit or fistula, the alignment system is removed leaving a guide wire in place over which a stent delivery system is deployed. A stent is then inserted to effectively form an end to end anastomosis after which the stent delivery system is removed.

A typical clinical procedure for creating the AVF according to one embodiment of the present invention is shown in FIGS. 8a to 8f. The example provided herein relates to the creation of an AVF in, or near, the wrist of a patient in need thereof. It will be appreciated that the AVF can be created in other locations within the body where relatively adjacent vessels are located.

The first step involves inserting a guide wire 18 into the appropriate artery 302 and the sensing catheter 100 into the appropriate vein 304 using any suitable technique, for example, the modified Seldinger technique (FIG. 8a) (see Rajan, Essentials of Percutaneous Dialysis Interventions, Springer (2011)).

Figure 8A:
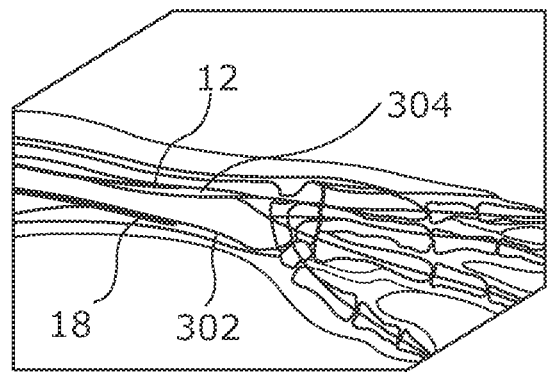

As best shown in FIG. 8a, the source catheter 10 is introduced over the guide wire 18 into the radial artery 302. Under suitable visualisation the catheters 10, 100 are advanced to the appropriate longitudinal position within the radial artery and cephalic vein. The visualisation may be by fluoroscopy. Alternatively, phased array ultrasound may be used to visualize the longitudinal position of the catheters.

Figure 8B:
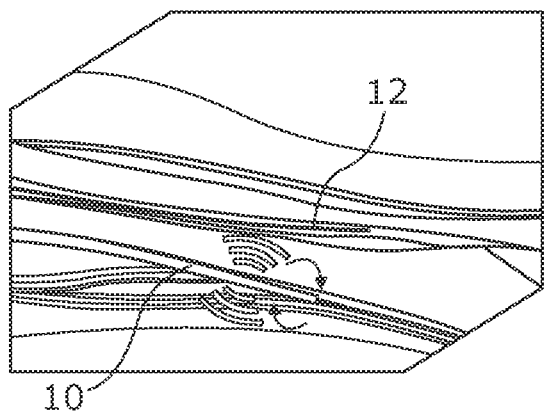
Figure 8C:
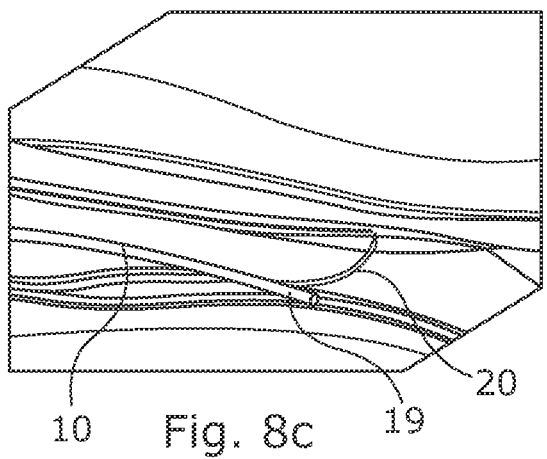
Figure 8D:
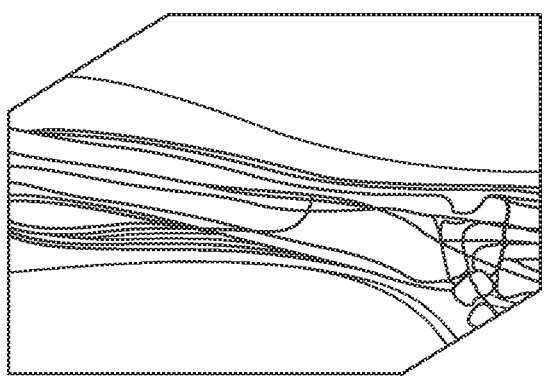
Figure 8E:
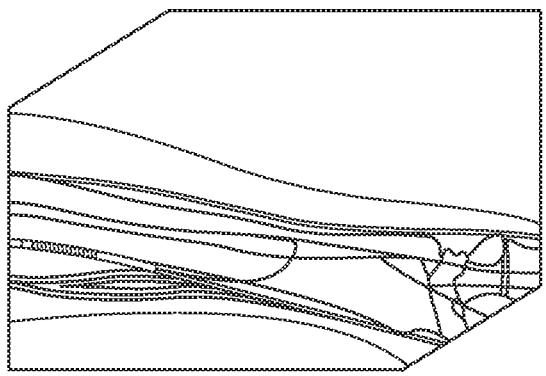
Figure 8F:
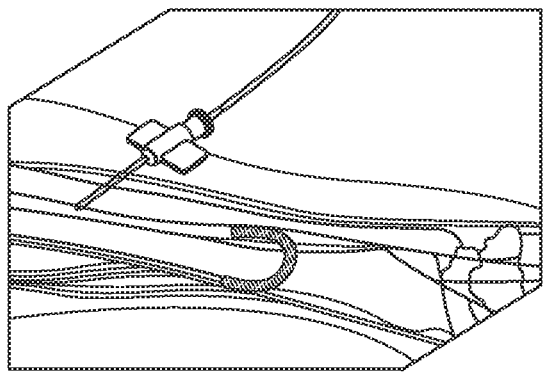

Once the source catheter 10 and the sensing catheter 100 are in place, the source catheter 10 is connected to the electronic alignment monitor system 200 via a cable 306 (not shown) from the sensing catheter 100 is connected to thereto. Optionally, the source catheter handle 30 (not shown) may now indicate to the clinician that they must calibrate the system by rotating the catheter through 360 degrees. Next, using both the electronic alignment monitor system 200 and fluoroscopy as a visual backup, the clinician operator rotates the source catheter so that the opening 19, where the needle 20 exits the lumen 38 of the source catheter 10, is aligned with the sensing electrode 108 (FIG. 8b). By "aligned" it is meant that the opening 19 points in a direction towards the sensing electrode 108. By directing the opening 19 towards the sensing electrode 108, a known field is defined between the adjacent vessels in which the conduit or fistula may be created. It will be appreciated that without the existence of such a known field the clinician operator would effectively be working without guidance and the risk of failure is increased substantially. Once proper alignment is achieved the guide wire 18 from the source catheter 10 is removed which releases and allows the needle 20 to be slowly advanced by the clinician operator, piercing through the arterial wall, through interstitial tissue and into the adjacent cephalic vein 304 (FIG. 8c). The direction of advancement of the needle—i.e. the needle track—is substantially along the alignment plane and within the known field. Once the needle 20 has crossed over successfully the clinician removes the sensing catheter 100 and inserts a longer guide wire 306 into the source catheter. This is advanced through the hollow core of the needle 20 and further into the vein 304 in the direction of blood flow (FIG. 8d). Once the guide wire 306 forms a secure U shape connecting the two vessels 302, 304 the source catheter 10 and needle 20 are retracted leaving the guide wire 306 in place. A typical stent delivery catheter system 308 is then advanced over the guide wire 306 (FIG. 8e). Finally, a covered stent graft 310 is deployed, effectively forming an end to end anastomosis (FIG. 8f). The fistula is left to mature while the vein 304 arterializes, and it is monitored for potential adverse effects like hematoma, internal bleeding or steal syndrome. The fistula thereby allows the vein to act as a future vascular access point for haemodialysis.

A further, more detailed, procedure specific to the vascular access application of the invention is provided below:

As a first step the patient undergoes duplex ultrasonography to determine if there is sufficient flow in the radial artery. An Allen test is then conducted with the aid of duplex ultrasonography to determine that there is sufficient ulnar flow to avoid steal syndrome.

The patient is then prepared for a lower arm interventional procedure. The catheter insertion site and the anastomosis site are sterilized and local anaesthetic is administered. Fluoroscopy is set up to image the lower arm. Alternatively, phased array ultrasound may be used to visualize the lower arm instead.

Next, a tourniquet is applied to the upper arm at just below the systolic pressure in order to ensure the veins in the lower arm do not collapse. Seldinger technique (see Rajan, Essentials of Percutaneous Dialysis Interventions, Springer (2011)) is performed using a micropuncture set in order to insert a venous guide wire into the cephalic vein slightly distal to the antecubital faucet. The sensing catheter 100 is advanced to the chosen anastomosis site which is slightly proximal to the wrist joint.

Seldinger technique is then performed using a micropuncture set in order to deploy a guide wire 18 into the radial artery followed by the insertion of a 7 F (0.092", 2.3 mm) sheath over the guide wire into the brachial artery near the antecubital faucet. The source catheter 10 is deployed over the guide wire and advanced so that it is in line with the sensing catheter 100 based on the fluoroscopy image. In this embodiment the guide wire is a 0.035" (3 F, 0.95 mm) guide wire, however, it should be appreciated that the guide wire may be of any suitable size The connector cable from the sensing catheter 100 is plugged into the electronic alignment monitor system 200, and the alignment signal monitored while the source catheter 100 is rotated until the alignment signal indicates optimum alignment. The electronic alignment monitor system 200 may be the handle 30, in which case the connector cable from the sensing catheter 100 is plugged into the handle 30. In one embodiment, the four indicator LED's will begin to blink yellow, indicating that sensing catheter 100 was connected correctly. The source catheter 10 is then clipped into the handle 30. The four indicator LED's will begin to blink green, indicating that source catheter 10 was connected correctly but that the apparatus needs to be calibrated.

The source catheter 10 is rotated 360 degrees by the clinician in order to calibrate the apparatus. Any suitable means of indicating calibration may be used, for example, visual, audible or tactile feedback may be employed to provide feedback to the clinician as correct calibration is achieved. In the present embodiment, all four indicator LED's will stop blinking indicating that the electronic alignment monitor system 200 has been calibrated correctly.

The source catheter 10 is then rotated by the clinician in order to align the apparatus correctly. Any suitable means of indicating alignment may be used, for example, visual, audible or tactile feedback may be employed to provide feedback to the clinician of the degree of alignment of the catheters 10, 100. In the present embodiment, the four LED's will light up one at a time a solid green. When all four LED's are lit the catheters 10, 100 are correctly aligned.

The clinician may then retract the guide wire 18 until a marker band is visible at the proximal end of the catheter 10 and the guide wire 18 is then locked into place. This indicates that the penetration member 20 can now be deployed. A syringe is attached to the proximal end of the penetration member 20. The penetration member 20 is then advanced by the clinician under fluoroscopy guidance to puncture out of the artery and into the cephalic vein. Flashback blood is collected into the syringe indicating that a successful puncture was made.

The guide wire 18 is advanced again through the penetration member 20 until it is sufficiently deployed within the vein in the prograde direction. The source catheter 10 and sensing catheter 100 are removed completely leaving only the guide wire 18 in place which crosses from artery to vein.

A 6 F stent graft delivery system may then be deployed over the guide wire that is left in place. The stent graft is advanced over the guide wire into the vein and is then deployed according to the manufacturers' instructions in order to create the AVF.

In an embodiment of the method, contrast medium is delivered to ensure there are no leaks. The tourniquet may then be removed. The delivery catheter may then also be removed followed by the removal of the introducer sheath. Pressure is then applied at the entry sites into the artery and the vein. Bandages are applied and the patient is prepped to leave the operating room.

Several anatomical sites are suitable for the creation of the fistula. Ultrasound studies indicate that sites such as the brachial artery and median cubital vein, the brachial artery and the cephalic vein, as well as the radial artery and cephalic vein are suitable locations for the current invention to be used in. In the specific embodiment of this invention, the radial artery and cephalic vein are to be used for creating a fistula.

In another application the source catheter 10 and the sensing catheter 100 are inserted into a coronary artery and vein using interventional techniques.

Using standard femoral access a standard guide catheter is inserted from the femoral artery, through the aorta to the coronary ostium. A guide wire is inserted into the coronary artery under fluoroscopic guidance. The source catheter 10 is deployed over the guide wire and advanced so that it is in line with the sensing catheter 100 based on the fluoroscopy image.

The sensing catheter 10 is inserted into the coronary vein by any suitable route, for example from the femoral vein, via the iliac veins to the inferior vena cava to the right atrium and via the coronary sinus to the coronary vein.

In this embodiment, the calibration of the apparatus and alignment of the catheters is generally as for the venous access application above.

Once alignment is optimized, as determined by the electronic alignment monitor system 200, the clinician retracts the guide wire 18 until a marker band is visible at the proximal end of the catheter 10 and the guide wire 18 is then locked into place. This indicates that the penetration member 20 can now be deployed. The penetration member 20 is then advanced by the clinician under fluoroscopy guidance to puncture out of the coronary artery and into the neighbouring coronary vein.

The guide wire 18 is advanced again through the penetration member 20 until it is sufficiently deployed within the vein. The source catheter 10 and sensing catheter 100 are removed completely leaving only the guide wire 18 in place which crosses from the artery to the vein.

A stent graft delivery system is deployed over the guide wire that is left in place. The stent graft is advanced over the guide wire into the vein and is then deployed according to the manufacturers' instructions in order to create an arteriovenous anastomosis between artery and vein in order to divert oxygenated blood to the vein.

In another embodiment of the invention, the source catheter is inserted into the popliteal artery or the tibial artery and the sensing catheter is inserted into the posterior tibial vein, in order to deliver an S-shaped graft from the artery to the vein that diverts blood to the lower limb extremities to treat critical limb ischaemia.

In this application, the calibration of the apparatus and alignment of the catheters is generally as for the venous access application described in more detail above.

Once alignment of the devices is optimized between popliteal artery/tibial artery and the posterior tibial vein, as determined by the electronic alignment monitor system 200, the clinician retracts the guide wire 18 until a marker band is visible at the proximal end of the catheter 10 and the guide wire 18 is then locked into place. This indicates that the penetration member 20 can now be deployed. The penetration member 20 is then advanced by the clinician under fluoroscopy guidance to puncture out of the artery and into the adjacent vein.

Where the penetration member comprises a hollow needle, a guide wire 18 is advanced again through the penetration member 20 until it is sufficiently deployed within the vein. The source catheter 10 and sensing catheter 100 are removed completely leaving only the guide wire 18 in place which crosses from the artery to the vein through the intervening tissue.

A stent graft delivery system is deployed over the guide wire that is left in place. The stent graft is advanced over the guide wire into the vein and is then deployed according to the manufacturers' instructions in order to create an arteriovenous anastomosis between artery and vein in order to divert oxygenated blood to the vein.

In yet another embodiment the methods and devices of the invention can be used in a Blalock-Taussig procedure in order to increase pulmonary blood flow for palliation in duct-dependent cyanotic heart defects such as pulmonary atresia. In this embodiment, the source catheter may be inserted into one branch of the subclavian artery or carotid artery and the sensor catheter is connected to the pulmonary artery. According to this embodiment the calibration of the apparatus and alignment of the catheters is generally as for the venous access application described in more detail above. The guide wire 18 may be advanced again through the penetration member 20 until it is sufficiently deployed within the target vessel. The source catheter 10 and sensing catheter 100 are removed completely leaving only the guide wire 18 in place which crosses from one vessel to the other. A Blalock-Taussig shunt is then deployed over the guide wire that is left in place between the two vessels and the guidewire withdrawn to leave the stable connection between the two vessels.

In another embodiment, a short 4 F (1.135 mm) introducer sheath may be placed into the left or right common femoral artery with a modified Seldinger technique and the source catheter is inserted through the sheath into the external iliac artery. An 11 F (11.52 mm) customised venous introducer is placed in the ipsilateral common femoral vein approximately 2 cm inferior to the arterial sheath insertion site and the sensor catheter is inserted into the distal external iliac vein. The source catheter 10 is then rotated by the clinician in order to align the apparatus of the invention correctly, as described in more detail above. The penetration member 20 is then advanced by the clinician, optionally under fluoroscopy or ultrasound guidance, to puncture out of the artery and into the cephalic vein. The guide wire 18 is advanced again through the penetration member 20 until it is sufficiently deployed within the vein. The source catheter 10 and sensing catheter 100 are removed completely leaving only the guide wire 18 in place which crosses from one vessel to the other.

A coupler or graft such as the ROX Coupler (ROX Medical, San Clemente, Calif., USA) is placed between the artery and the vein in the pelvic area to create an anastomosis—a passage through which blood can flow. This anastomosis, or passage, reduces the peripheral vascular resistance and may lower arterial blood pressure in hypertensive patients.

In another embodiment of the invention, the source catheter 10 may be inserted into the sub-intimal space of an artery with a total occlusion, the insertion is over an existing guide wire that has been previously inserted into the space. The sensing catheter 100 is inserted into the same artery from a site distal to the occlusion. The source catheter 10 is advanced past the occlusion, and is rotated by the clinician in order to align the apparatus correctly towards the sensing catheter and thus back into the true lumen of the artery. In a variant of the method for this application the sensing catheter 100 is inserted into a vein that runs parallel to the artery. The source catheter 10 is inserted past the occlusion, and is rotated by the clinician in order to align the apparatus correctly towards the sensing catheter. The source catheter is rotated by 180° so the alignment signal indicates the source catheter is facing away from the vein, and thus back into the true lumen of the artery. In both variants of the method the penetration member 20 is then advanced by the clinician, optionally under fluoroscopy or ultrasound guidance, to puncture out of the subintimal space and into the true lumen of the artery. The guide wire 18 is advanced again through the penetration member 20 to re-enter the artery. The source catheter 10 and sensing catheter 100 are removed completely leaving only the guide wire 18 in place which crosses from one chamber to the other. An angioplasty balloon and stent can then be deployed over the guide wire to form a blood channel through the sub-intimal space around the occlusion.

It will be appreciated that in another embodiment of the invention the system and apparatus may be utilised for general laparascopic procedures. In this embodiment, the source catheter 10 and the sensing catheter 100 are inserted into neighbouring vessels, chambers, ventricles or cavities via a percutaneous vascular route or though a trochar using standard laparascopic techniques.

In this embodiment, the calibration of the apparatus and alignment of the catheters is generally as for the venous access application described in more detail above.

Once alignment is optimized, as determined by the output of the electronic alignment monitor system 200, the penetration member 20 is then advanced by the clinician under fluoroscopy guidance to puncture out of one chamber and into the neighbouring chamber.

The guide wire 18 is advanced again through the penetration member 20 until it is sufficiently deployed within the target chamber. The source catheter 10 and sensing catheter 100 are removed completely leaving only the guide wire 18 in place which crosses from one chamber to the other. The guide wire can then be used to guide the deployment of a catheter which can be used to install, for example, a trans-chamber device, such as a stent graft, a valve, an intra-septal device or a pressure sensor.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

REFERENCES

J. J. P. M. Leermakers, A. S. Bode, A. Vaidya, F. M. van der Sande, S. M. A. A. Evers, and J. H. M. Tordoir, "Cost-effectiveness of Vascular Access for Haemodialysis: Arteriovenous Fistulas Versus Arteriovenous Grafts," European Journal of Vascular & Endovascular Surgery, vol. 45, no. 1, pp. 84-92, January 2013.

Department of Health and Human Services, Health Resources and Services Administration, Healthcare Systems Bureau, Division of Transplantation, "2014 Annual Report of the U.S. Organ Procurement and Transplantation Network and the Scientific Registry of Transplant Recipients," University Renal Research and Education Association, Ann Arbor, 2014.

A. A. Al-Jaishi, Oliver, S. M. Thomas, C. E. Lok, A. X. G. M., S. D. K., R. R. Q, and L. M. M., "Patency Rates of the Arteriovenous Fistula for Hemodialysis: A Systematic Review and Meta-analysis," YAJKD, vol. 63, no. 3, pp. 464-478, March 2014.

Rajan, Essentials of Percutaneous Dialysis Interventions, 2011, Springer

Dimitris C L 2008 *Shape Memory Alloys: Modelling and Engineering Applications* (Berlin: Springer)

Melvin D Lobo et. Al. 'Central arteriovenous anastomosis for the treatment of patients with uncontrolled hypertension (the ROX CONTROL HTN study): a randomised controlled trial' The Lancet Volume 385, No. 9978, p 1634-1641, 25 Apr. 2015

What is claimed is:

1. A method of connecting two adjacent vessels within the body of a patient, said method comprising the steps of:
    a) introducing a first source device into a first vessel, the first device comprising at least one signal electrode for generating an asymmetric electric field;
    b) introducing a second sensing device into a second vessel, the second device comprising at least one detector for detecting the asymmetric electric field;
    c) aligning the first and second device relative to each other based on the asymmetric electric field generated by the first device that is detected by the detector on the second device;
    d) forming a conduit between the first vessel and the second vessel; and
    e) removing the first and second devices to leave the first and second vessels connected via the conduit.

2. The method of claim 1, wherein the first device comprises a catheter.

3. The method of claim 1, wherein the second device comprises a catheter.

4. The method of claim 1, wherein the alignment of the first and second device is determined by the amplitude of the asymmetric electric field as detected by the detector on the second device.

5. The method of claim 4, wherein the optimal alignment of the first and second device is at a maxima or minima of the amplitude of the asymmetric electric field detected by the detector on the second device.

6. The method of claim 1, further comprising an additional step between step (b) and step (c) of calibrating the first and second devices.

7. The method of claim 6, wherein the calibration comprises rotating the first device between 0 to 360° with respect to the second device.

8. The method of claim 1, wherein the conduit between the first vessel and the second vessel is formed by a penetrating member.

9. The method of claim 8, wherein the penetrating member comprises a needle.

10. The method of claim 9, wherein the needle is retained within the first device prior to deployment to form the conduit.

11. The method of claim 9, wherein the needle is retained within the second device prior to deployment to form the conduit.

12. The method of claim 10, wherein the conduit between the first vessel and the second vessel is formed by advancing the needle in a radial direction outwardly from the first device.

13. The method of claim 11, wherein the conduit between the first vessel and the second vessel is formed by advancing the needle in a radial direction outwardly from the second device.

14. The method of claim 13, wherein the advancement of the needle is guided by a monitoring system external to the body of the patient.

15. The method of claim 14, wherein the monitoring system is selected from fluoroscopy and phased array ultrasound.

16. The method of claim 1, further comprising installing a trans-vessel device in order to stabilise the conduit, wherein between steps (d) and (e) a guide wire is advanced through the conduit, the guide wire being left in place when the first and second device are removed, and following step (e) a trans-vessel device is installed over the guide wire.

17. The method of claim 16, wherein the trans-vessel device comprises a stent.

* * * * *